(12) United States Patent
Juang et al.

(10) Patent No.: US 6,814,963 B2
(45) Date of Patent: Nov. 9, 2004

(54) BACULOVIRUS-BASED EXPRESSION SYSTEM

(75) Inventors: Jyh-Lyh Juang, Taipei (TW); Dung-Fang Lee, Tainan (TW)

(73) Assignees: National Health Research Institutes, Taipei (TW); Alarvita Biolife Corporation, Taipei (TW)

( * ) Notice: Subject to any disclaimer, the term of this patent is extended or adjusted under 35 U.S.C. 154(b) by 20 days.

(21) Appl. No.: 10/050,665

(22) Filed: Jan. 16, 2002

(65) Prior Publication Data

US 2003/0022377 A1 Jan. 30, 2003

Related U.S. Application Data

(60) Provisional application No. 60/277,893, filed on Mar. 23, 2001.

(51) Int. Cl.$^7$ .................... A61K 48/00; C12N 15/866; C12N 15/63; C12Q 1/70; C12P 21/00

(52) U.S. Cl. .................... 424/93.2; 424/93.1; 424/93.6; 536/23.1; 536/23.2; 536/24.1; 435/320.1; 435/235.1; 435/5; 435/6; 435/69.1; 435/29; 435/455; 435/456; 435/325; 435/348; 435/366; 435/252.3

(58) Field of Search ................ 435/320.1, 235.1, 435/5, 6, 69.1, 29, 455, 456, 325, 348, 366, 252.3; 536/23.1, 23.2, 24.1; 424/93.1, 93.2, 93.6

(56) References Cited

U.S. PATENT DOCUMENTS 5,004,687 A 4/1991 Miller ...................... 435/69.1

6,589,783 B2 * 7/2003 Novy et al. .............. 435/320.1

OTHER PUBLICATIONS

Condreay, et al., "Transient and Stable Gene Expression in Mammalian Cells Transduced With a Recombinant Baculovirus Vector", *Proc. Nat'l Acad. Sci.*, vol. 96: 127–132 (1/99).

Morris, et al., "Characterization of Productive and Non–productive ACMNPV Infection in Selected Insect Cell Lines", *Virology*, vol. 197: 339–348 (1993).

* cited by examiner

*Primary Examiner*—David Guzo
(74) *Attorney, Agent, or Firm*—Fish & Richardson P.C.

(57) ABSTRACT

Compositions and methods are provided that relate to a recombinant virus-based vector, e.g., a baculovirus-based vector, that allows the expression of an exogenous target protein in non-permissive cells (e.g., non-permissive insect cells or mammalian cells) in the absence of expression of a detectable selection marker. The vector includes a nucleic acid sequence encoding a detectable selection marker which is controlled by a promoter that is active in host cells used to screen for recombinant virus but is silent in the non-permissive cell used for expression of the exogenous target protein. The vector also includes an exogenous nucleic acid sequence encoding a target protein under the control of a promoter that is active in the non-permissive cell. This system allows the selection marker to be expressed during viral plaque screening, but not while the target protein is being produced.

25 Claims, 2 Drawing Sheets

BACULOVIRUS-BASED EXPRESSION SYSTEM

RELATED APPLICATIONS

This application claims the benefit of U.S. Provisional Application Ser. No. 60/277,893, filed Mar. 23, 2001, which is hereby incorporated by reference in its entirety.

BACKGROUND

The baculoviruses are a family (Baculoviridae) of DNA viruses which primarily infect insects of the order *Lepidoptera* in nature. Baculoviruses have been used to express exogenous genes in insect cells for some time. One of the most studied baculoviruses is the *Autographa californica* multiple nuclear polyhedrosis virus (AcMNPV).

Baculoviruses can express large quantities of exogenous (non-baculovirus) proteins driven by the endogenous polyhedrin and p10 promoters, both of which are strongly active during the late stage of the natural life cycle of baculoviruses. Although the natural host spectrum of baculovirus is often defined in terms of the ability of the virus to replicate in a given cell, baculovirus can penetrate and express genetic materials in non-natural (non-permissive) host cells, e.g., mammalian cells (see, e.g., Hofmann et al., 1995, Proc. Natl. Acad. Sci. USA 92, 10099–10103; Boyce et al., 1996, Proc. Natl. Acad. Sci. USA 93, 12348–2352; Shoji et al., 1997, J. Gen. Virol. 78, 2657–2664; and Yap et al., 1997, Virology 231, 192–200) and *Drosophila* cells (Pennock et al., 1984, Mol. Cell Biol. 4, 399–406).

Conventional baculovirus expression systems offer the advantages that a) baculoviruses are not normally pathogenic to humans; b) the viruses can be propagated in serum-free media and grown to a titer of over $10^8$ pfu/ml; and c) the genome of the virus (approximately 80 to 230 kb) accepts large exogenous DNA molecules. The conventional baculovirus expression system is limited in that a) protein expression can result in cell-lysis; and b) when one baculovirus infects its host for a period of time, the entrance of another baculovirus into the same host (successive infection) becomes non-permissive. Because successive infection (superinfection) is not permissible, it is impossible to utilize a conventional baculovirus to express two or more genes in its host cells at different times.

SUMMARY

The present invention is based on the development of a recombinant virus-based vector, e.g., a baculovirus-based vector, that allows the expression of an exogenous target protein in non-permissive cells (e.g., non-permissive insect cells or mammalian cells) in the absence of expression of a detectable selection marker. The baculovirus-based vector includes a nucleic acid sequence encoding a detectable selection marker which is controlled by a promoter that is active in host cells (e.g., Sf21 or Sf9 cells) used to screen for recombinant virus but is silent in the non-permissive cells (e.g. *Drosophila* cells and mammalian cells) used for expression of the exogenous target protein. The vector also includes an exogenous nucleic acid sequence encoding a target protein under the control of a promoter that is active in the non-permissive cell but inactive in host cells. This system allows the selection marker to be expressed during viral plaque screening, but not while the target protein is being produced. Further, a recombinant virus according to the invention is able to successively infect a non-permissive insect host cell, permitting the expression of a plurality of target proteins in the same non-permissive insect cell.

Accordingly, in one aspect, the invention features a recombinant virus, e.g., a baculovirus, which includes a first nucleic acid sequence encoding a detectable marker operably linked to a first promoter that is active in a host cell culture and is inactive in a non-permissive cell; and also includes a second nucleic acid sequence encoding an exogenous protein operably linked to a second promoter, which second promoter is active in the non-permissive cell.

In another aspect, the invention features a method for selecting a viral plaque, e.g., for infection of a non-permissive cell. The method includes: providing a recombinant virus, e.g., a baculovirus, capable of infecting the non-permissive cell, which virus includes a first nucleic acid sequence encoding a detectable marker operably linked to a promoter that is active in a host cell but is silent in the non-permissive cell; and a second nucleic acid sequence comprising an exogenous nucleic acid sequence operably linked to a second promoter, wherein the second promoter is active in the non-permissive cell; infecting a host cell culture with the recombinant baculovirus; and identifying a viral plaque by detecting expression of the detectable marker.

In another aspect, the invention features a method for producing a protein in a non-permissive cell. The method includes: providing a recombinant virus, e.g., a virus described herein, e.g., a baculovirus described herein; infecting a host cell culture with the recombinant virus; selecting a viral plaque by identifying expression of the detectable marker; amplifying the virus from the selected viral plaque; and infecting a non-permissive cell with the amplified virus. The non-permissive cell thereby produces the protein encoded by the exogenous nucleic acid sequence and does not express the detectable marker.

In a preferred embodiment, the non-permissive cell is infected in vitro. In another preferred embodiment, the non-permissive cell is infected in vivo. Preferably, the method further includes the step of re-infecting a non-permissive cell, e.g., a non-permissive insect cell, with a recombinant virus, e.g., the same or a different virus described herein. This method provides a superinfection system that allows the expression of a plurality of proteins in the same host cell. This system is thereby useful in a two-hybrid screening assay.

In each of the aspects of the invention, a preferred recombinant virus described herein is a baculovirus.

In preferred embodiments, a non-permissive cell described herein is an insect cell, e.g., a *Drosophila* cell (e.g., an S2 cell or Kc cell) or a mosquito cell (e.g., a C6/36 cell); or a mammalian cell (preferably a human cell, e.g., a human primary cell or an established cell line). Preferred promoters that are active in a host cell and inactive in a non-permissive cell include, e.g., the viral polyhedrin promoter or the P10 viral promoter. Preferred promoters that are active in a non-permissive cell, e.g., a mammalian cell, can include, e.g., a CMV promoter, a RSV promoter, or a SV40 promoter. Other preferred promoters that are active in a non-permissive cell, e.g., an insect cell, include a heat shock protein promoter (e.g., hsp7O), a *Oravia pseudotsuciata* nuclear polyhedrosis virus immediate early promoter, an OP1E2 promoter, a MT promoter, or an actin 5C promoter. The detectable marker is preferably a fluorescent protein, e.g., a green fluorescent protein (GFP) or an enhanced GFP (EGFP).

As used herein, the term "exogenous nucleic acid sequence" refers to any nucleic acid sequence that is not part of the virus genome in nature. Such a sequence can include a nucleic acid sequence that is normally present in the non-permissive cell to be infected. Also included is a sequence that is not normally present in the non-permissive cell to be infected (e.g., related and/or unrelated genes of other cells and of other species). The term "non-permissive" when referring to a cell means that the cell does not permit replication of a virus described herein and does not permit the virus to enter the lytic phase within the cell. Such non-permissive cells can nonetheless be infected with a virus described herein and can produce a protein encoded by a nucleic acid sequence of the virus. By "operably linked" is meant a functional linkage between a promoter and a second nucleic acid sequence, wherein the promoter sequence can initiate and/or mediate transcription of the DNA sequence corresponding to the second sequence. Operably linked sequences can be contiguous and, where necessary to join two protein coding regions, contiguous and in the same reading frame. A "protein" or a "target protein" refers to a peptide of any length.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
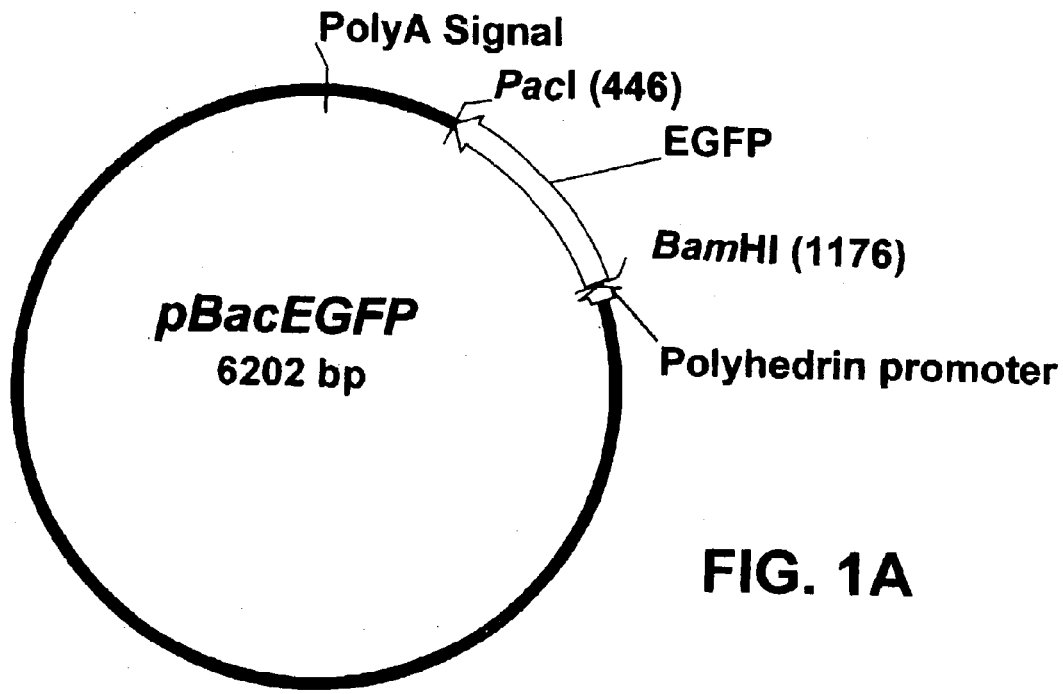
FIG. 1 (Parts A–D) illustrates the map of the baculovirus transfer vectors (A) pBacEGFP, (B) pBacEGFP/CMV DsRed (C) pBacEGFP/hsp70 EGFP and (D) pBacEGFP/actin5C EGFP.

The baculovirus expression methods described herein allow the expression of a target protein in a non-permissive cell, e.g., a non-permissive insect cell or mammalian cell. The target protein can be expressed in the absence of the expression of a selection marker. A detectable selection marker is only expressed during the viral plaque screening step as the marker is expressed via a promoter that is silent in the non-permissive cells used for target protein expression.

A detectable marker useful in the viruses and methods described herein can include any reporter molecule that is detectable, e.g., by virtue of having an enzymatic, chromogenic, fluorescent, or luminescent property. Useful detectable markers include fluorescent proteins, e.g., GFP, EGFP, and DsRed (Matz et al. *Nat. Biotechnology.* 17:969–973); luciferase; chloramphenicol acetyl transferase (CAT); β-galactosidase; β-lactamase; or secreted placental alkaline phosphatase. Other reporter molecules and other enzymes whose function can be detected, e.g., by appropriate chromogenic or fluorogenic substrates, are known in the art.

Further, the baculovirus-based expression methods described herein allow the superinfection of an insect cell. There was no interference to protein expression by successive infection with two homologous baculoviruses. Thus, it is possible to utilize the present invention as a powerful method to express multiple proteins in a non-yeast system. This property of the present viruses and methods is useful in performing two-hybrid screens as described below.

Baculovirus

The recombinant viruses described herein are engineered to express an exogenous target protein (e.g., a therapeutic protein) in a non-permissive cell, e.g., an insect cell or a mammalian cell. Preferably, the recombinant virus is part of a non-lytic system for producing recombinant proteins.

A preferred virus for use in the claimed methods is the baculovirus AcMNPV. Other examples of baculoviruses that can be used include, but are not limited to, *Bombyx mori* nuclear polyhedrosis virus, *Orgyia pseudotsugata* mononuclear polyhedrosis virus, *Trichoplusia ni* mononuclear polyhedrosis virus, *Heliothis zea* baculovirus, *Lymantria dispar* baculovirus, *Cryptophlebia leucotreta granulosis* virus, *Penaeus* monodon-type baculovirus, *Plodia interpunctella granulosis* virus, *Mamestra brassicae* nuclear polyhedrosis virus, or *Buzura suppressaria* nuclear polyhedrosis virus.

Standard procedures for engineering baculoviruses having various foreign genetic elements are well known in the art. Procedures for introducing recombinant baculoviruses into insects or cells thereof are also well known. See, e.g., Pfeifer et al., 1997, Gene 188:183–190; and Clem et al., 1994, J Virol 68:6759–6762.

If desired, the baculovirus genome can be engineered to carry a human origin of replication. Such sequences have been identified, e.g., in Burhans et al., 1994, Science 263:639–640, and can facilitate replication in human cells. Other origins of replication, such as the Epstein-Barr Virus replication origin and trans-acting factor, can facilitate gene expression in human cells. Optionally, the virus can be engineered to express more than one exogenous gene. If desired, the virus can be engineered to facilitate targeting of the virus to certain cell types. In addition, the virus can be chemically modified to target the virus to a particular receptor.

If desired, the baculovirus can be engineered so that its growth is defective in its host cell. Such a strain of baculovirus can provide added safety and can be propagated on a complementing packaging line. An example of a defective baculovirus is one in which an immediate early gene, such as IE1, has been deleted. This deletion can be made by targeted recombination in yeast, and the defective virus can be replicated in insect cells in which the IE1 gene product is supplied.

Non-Permissive Cells

The hosts of the recombinant baculovirus according to this invention may vary depending on the designs of systems or consideration of specificity. Selection and determination of a proper host for the recombinant baculovirus and methods described herein are within the knowledge and techniques available to persons skilled in the art. The hosts suitable for the recombinant baculovirus according to this invention may include, but are not limited to, the cells derived from species ranging from insects to vertebrates. Preferred hosts are insect-derived cells and mammalian cells.

The insect-derived cells suitable for target protein expression according to this invention include cells derived from the insect group, preferably the insect continuous cell lines, such as S2 cells, Kc cells, and C6/36 cells. The mammalian cells suitable for the recombinant baculovirus according to this invention include primary cells, e.g., human primary cells, and cell lines from mammalian species, such as cell lines from murine, rat, porcine or human sources.

Expression of Target Proteins

The recombinant viruses and methods described herein are useful for expressing a target protein in a wide range of cells, e.g., non-permissive cells as described herein. Preferred target proteins are therapeutic proteins. For example, the present invention can be used to express in a subject (e.g., a mammal, such as a human) a nucleic acid sequence encoding a protein which corrects a deficiency in gene expression. Examples of types of therapeutic proteins that are candidates for expression using the methods described herein include vaccines, antibodies, biologically active peptides, cytokine and receptors thereof, growth factors and receptors thereof, phosophodiesterases, metabolic enzymes, kinases, phosphatases, tumor antigens, viral envelop, viral core, virus-like particles, surface antigens.

The present invention can also be used to facilitate the expression of a target protein in a cell having no obvious deficiency. For example, the present invention can be used to express a physiologically essential factor (e.g., a hormone or a growth factor) in a cell of a subject in order to supply the subject with the factor. The present invention can also be used to express a regulatory gene or a gene encoding a transcription factor in a cell to control the expression of another gene. If desired, tumor suppressor genes (e.g., p53, Rb) can be expressed in a cell in a method of treating cancer. Other useful gene products include RNA molecules for use in RNA decoys, antigens, or ribosome-based methods of inhibiting gene expression. If desired, the present invention can be used to express a gene, such as cytosine demeans, whose product will alter the activity of a drug or prodrug, such as 5-fluorocytosine, in a cell.

Preferred genes for expression include those genes that encode proteins that are expressed in normal cells. Subcloning these genes into a baculovirus can be readily accomplished with common molecular biology techniques.

In particular, for administration to a mammal, the baculovirus can be formulated into pharmaceutical compositions by admixture with pharmaceutically acceptable non-toxic excipients and carriers (e.g., saline). In practicing the present invention in a mammal (such as a human), the baculovirus can be prepared for use in parenteral administration (e.g., for intravenous injection, intra-arterial injection, intraperitoneal injection, intrathecal injection, direct injection into an area (e.g., intramuscular injection), particularly in the form of liquid solutions or suspensions. The baculovirus can also be prepared for intranasal or intrabronchial administration, particularly in the form of nasal drops or aerosols. In another method of practicing the present invention, the baculovirus is used to infect a cell outside of the subject to be treated, and the infected cell then is administered to the subject to be treated. In this method, the cell can be autologous or heterologous to the mammal to be treated. The cell is cultured and infected with the baculovirus using the guidance provided herein in combination with what is known in the art (see, e.g., Grossman et al., 1994, Nature Genetics 6: 335). The cell can then be administered to the subject by injection (e.g., into the peritoneal cavity or by intravenous injection).

The amount of baculovirus or number of infected cells to be administered to a subject and the frequency of administration are dependent upon a variety of factors such as the sensitivity of methods for detecting expression of the exogenous gene, the strength of the promoter used, the severity of the disorder to be treated, and the target cell(s) of the virus. Generally, the virus is administered at a multiplicity of infection (moi) of about 0.1–800; preferably, the moi is about 5–200; more preferably, the moi is about 10–100.

Delivery of a baculovirus to a cell and expression of the exogenous gene can be monitored using standard techniques for assaying gene expression. For example, delivery of AcMNPV to a cell can be monitored by detecting AcMNPV DNA or RNA (with or without amplification by PCR) by common procedures such as Southern or Northern blotting, slot or dot blotting, or in situ hybridization. Suitable probes which hybridize to nucleic acids of AcMNPV, the promoter or the exogenous gene can be conveniently prepared by one skilled in the art of molecular biology.

Expression of an exogenous gene in a cell can be followed by assaying a cell or body fluid (e.g., serum) obtained from the subject having the cell for RNA or protein corresponding to the gene. Detection techniques commonly used by molecular biologists (e.g., Northern or Western blotting, in situ hybridization, slot or dot blotting, PCR amplification, SDS-PAGE, immunostaining, RIA, and ELISA) can be used to measure gene expression.

The therapeutic effectiveness of expressing an exogenous gene in a cell can be assessed by monitoring the subject having the cell for known signs or symptoms of a disorder. Parameters for assessing treatment methods are known to those skilled in the art of medicine.

Two Hybrid System

The yeast two-hybrid system is a widespread application for identification of interaction partners or detection of protein-protein interactions in yeast (*Saccharomyces cerevisiae*) cells. A two-hybrid system based on higher eukaryotic cells can be a powerful complementary approach to verify protein interaction partners obtained from a yeast two-hybrid system screening. As the baculovirus-based expression methods described herein allow for the superinfection of non-permissive cells, these methods provide an efficient gene transfer vehicle for introducing multiple exogenous proteins in the same host cell. Therefore, the methods described herein are useful for performing two-hybrid screens in the context of higher eukaryotic cells, e.g., non-permissive cells such as insect cells or mammalian cells.

The two-hybrid method uses the restoration of transcriptional activation to indicate the interaction between two proteins. As an example of a yeast-based two-hybrid system, the yeast GAL4 transcriptional activator, for example, contains a DNA-binding domain (DNA-BD) and a transcriptional activation domain (AD). Two different cloning vectors are used to generate separate fusions of these GAL4 domains to genes encoding proteins that potentially interact with each other. The recombinant hybrid proteins are co-expressed in yeast reporter strains and are targeted to the yeast nucleus. If the target- and candidate-protein portions of the two hybrids interact with each other, the DNA-BD will be tethered to its AD. Thus, as a result of a two-hybrid interaction, the GAL4 transcriptional activator will be functionally reconstituted and will activate transcription of reporter genes (e.g., lacZ, HIS3, β-galactosidase, luciferase, or EGFP) having upstream GAL4 binding sites. This makes the protein interaction phenotypically detectable. A mammalian two-hybrid system works similarly, except that different AD (such as VP16 protein of herpes simplex virus) and reporter genes (such as CAT) are employed. Basic techniques for performing such assays are known in the art.

The two-hybrid method according to the present invention involves introducing into a cell, at same or difference times, multiple recombinant baculoviruses whose genomes carry exogenous nucleic acid sequences encoding target proteins, allowing the cell to live under conditions such that the exogenous sequences are expressed, and monitoring the interactions between/among the proteins encoded by the exogenous sequences. Since a cell harboring the recombinant baculovirus does not enter a lytic phase and can be successively infected at different times, the two-hybrid method according to the present invention renders the introduction of recombinant baculoviruses into the cell more convenient and flexible, and much more, the advantageous introduction of recombinant viruses at different times. One advantage of this method is that it enables not only identification of interacting proteins, but also results in the immediate availability of the cloned genes for these proteins. In addition, the two-hybrid method often detects weak and transient interactions. Neither purified target proteins nor antibodies are required. The assay is performed in vivo, so that the proteins being tested are more likely to be in their native conformations. The two-hybrid method can be used to determine if two known proteins (for which corresponding genes have been cloned) interact. Once two proteins have been shown to interact, further analysis can pinpoint the regions that are directly involved in the interaction. Another important application of the two-hybrid method is to identify previously unknown proteins that interact with a target protein.

EXAMPLES

Example 1

Construction and Production of Recombinant Baculovirus for Expression in Mammalian Cells A mammalian-baculovirus shuttle vector was designed to adopt EGFP as a detectable marker (viral plaque selection marker) under the control of polyhedrin promoter as in host cells. The polyhedrin promoter is silent in non-permissive cells. For easy illustration and detection of the target gene expression in non-permissive cells, an expression cassette encompassing a red fluorescent DsRed gene from sea anemone was constructed under the control of CMV-IE promoter. In this example, DsRed is merely illustrative of numerous target proteins that can be expressed using the methods described herein. The recombinant baculovirus of the invention was constructed by using shuttle vectors derived from pBacPAK8 (Clontech).

First, pBacEGFP was constructed by cloning a nucleotide sequence encoding a detectable marker (a PCR product of EGFP) into pBacPAK8 using Bam HI and Pac I sites. The EGFP fragment was PCR amplified from pEGFP-1 (Clontech) with primers, 5'-CAGGATCCGCCACCATGGTGAGCAAGGGCG-3' (SEQ ID NO:1), and 5'-AGCAATTAATTAATGAACATGTCGAGCAGGTAC-3' (SEQ ID NO:2).

Figure 1B:
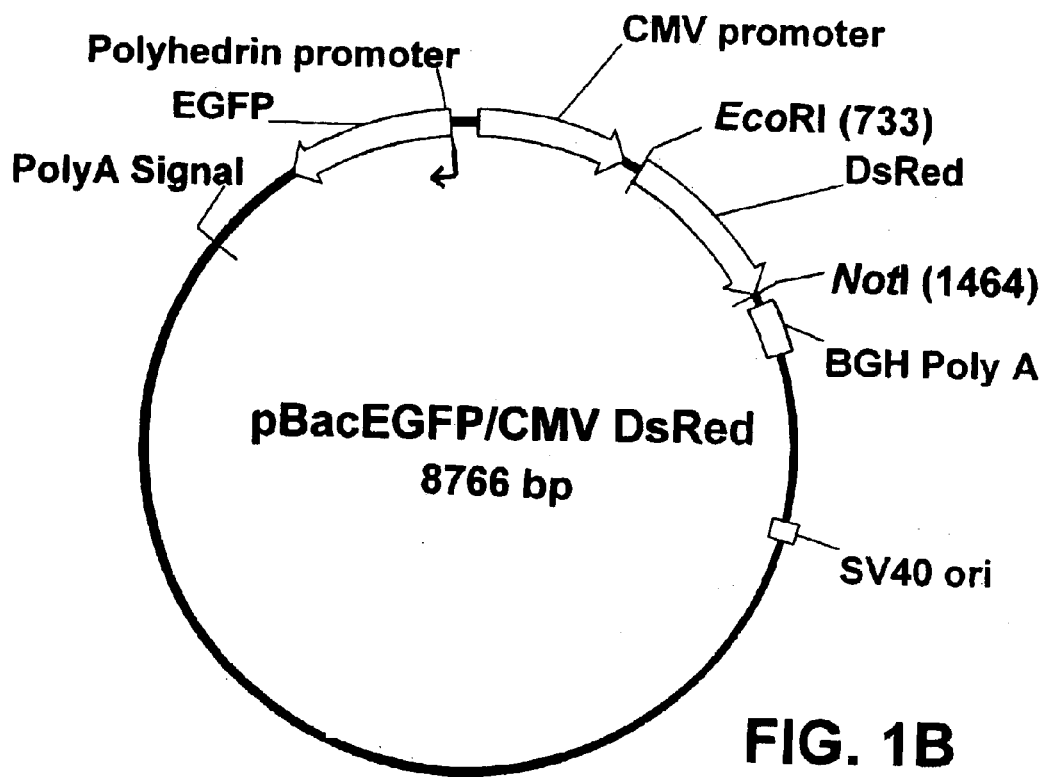

Second, A 2.6-kb Nru I and Stu I fragment from pcDNA3 (Invitrogen) (containing CMV-IE promoter with a multiple cloning site polyadenylation signal followed by SV40 origin of replication) was inserted into the pBacEGFP in EcoR V site as pBacEGFP/CMV. The shuttle vector pBacEGFP/CMV DsRed contained DsRed as the target gene from pDsRed-N1 (Clontech) and was inserted into the EcoR I and Not I sites of pBacEGFP/CMV. The resulting baculovirus-mammalian shuttle vector, pBacEGFP/CMV DsRed, is depicted in FIG. 1(B).

Recombinant baculoviruses (BacEGFP/CMV DsRed) were generated by the BacPAK system (Clontech) and amplified by propagating them in *S. frugiperda* (fall armyworm) Sf21 cells (a permissive cell line) by routine techniques. Through fluorescence microscopy, recombinant viruses could readily be identified by screening for green fluorescence signal emitted from the infected Sf21 cells. This visible marker not only significantly facilitated the screening of recombinant virus in host cells but also avoided the cumbersome staining procedure of neutral red dye, which could be a putative mutagen to recombinant baculovirus.

Example 2

Transduction of Non-Permissive Mammalian Cells by Recombinant Baculovirus and Detection of Target Protein Expression HeLa and Cos-1 cells maintained using conventional cell culture techniques were seeded in 6-well culture dishes at $2 \times 10^5$ cells per well. Culture medium was removed and replaced with virus inoculum prepared as in Example 1 at 100 multiplicity of infection (moi). Infected cells were incubated with 40 rpm shaking for 1 hr at 37° C. After viruses were removed from the culture, fresh medium with 1 mM Trichostatin (TSA) (identified as a histone deacetylase inhibitor) was added to the cells and incubated at 37° C. for another 24 hr.

After 24 hr incubation, cell cultures were examined for EGFP and DsRed expressions by confocal microscopy and Western blot analysis. By confocal fluorescence microscopy, both HeLa and Cos-1 cells displayed a wide range of target protein DsRed expression but no EGFP signal (the plaque assay selection marker) was detected. This finding was confirmed by Western blot analysis of membranes of the recombinant virus-transduced cell extracts probed with antibodies directed against either EGFP or DsRed. EGFP was detected by a GFP polyclonal antibody (Clontech, catalog number: 8363–2)

These data clearly suggest that the EGFP selection marker was silent in mammalian cells and only the target gene was expressed under the control of CMV-IE. These examples demonstrate a very convenient plaque assay method for baculovirus-mediated protein expression in mammalian cells. The visible EGFP selection maker significantly simplifies and facilitates the operation of plaque selection and virus titer determination. In particular, these examples indicate that the host specific expression of a selection marker can eliminate possible competition and interference with the target gene expression in mammalian cells.

Example 3

Superinfection of Mammalian Cells with Recombinant Baculoviruses

To estimate whether mammalian cells infected with one baculovirus would shut down the infection and protein expression of another baculovirus or not, HeLa cells were co-infected with BacEGFP/CMV DsRed and BacEGFP/CMV EGFP or sequentially infected by the aforementioned two viruses at 4-h intervals. EGFP was detected by a GFP polyclonal antibody (Clontech, catalog number: 8363–2); DsRed was detected by a DsRed polyclonal antibody (Clontech, catalog number: 8370–1). After 36 hr incubation, cell extracts were analyzed by Western blots probed with antibodies directed against EGFP and DsRed. No obvious differences were found between single baculovirus infection, confection or infection sequential with two baculovirus as in HeLa cells. No interference to protein expression was found by successive infection with two baculoviruses. Confocal microscopy of fluoresent target gene co-expression in S2 cells. BacEGFP/CMV DsRed and BacEGFP/CMV EGFP were either co-infected or sequentially infected at 4-h intervals. More than 96% of the cells demonstrated co-expression of two proteins either by co-infection or by superinfection of recombinant viruses.

Example 4

Construction and Production of Recombinant Baculovirus for Expression in Non-Permissive Insect Cells Recombinant Virus Carrying EGFP Gene Driven by Polyhedrin Promoter In this example, an EGEP gene was positlone under the control of a polyhernn promoter. This promoter is active in Sf21 cells but silent in *Drosophila* S2 cells. EGFP was used as a reporter gene to estimate transfection efficiencies and relative protein expression levels. The plasmid pBacEGFP was constructed by subcloning a EGFP PCR product into pBacPAK8 (Clontech) at Barn HI and Pac I sites and the EGFP PCR product was amplified from pEGFP-1 (Clontech) with specific primers. The primers used for PCR were as follows:

5EGFP/Bam HI:
5'CAGGATCCGCCACCATGGTGAGCAAGGGCG (SEQ ID NO:1) ; and
3EGFP/Pac I:
3'TCGTTAATTAATTACTTGTACAGCTCGTCCATG (SEQ ID NO:3).

Plaques were screened and picked and titers were calculated by visualizing EGFP-expression by fluorescence microscopy as described above.

Recombinant Virus Carrying EGFP Gene Driven by Promoters that are Active in Non-Permissive Insect Cells.

Figure 1C:
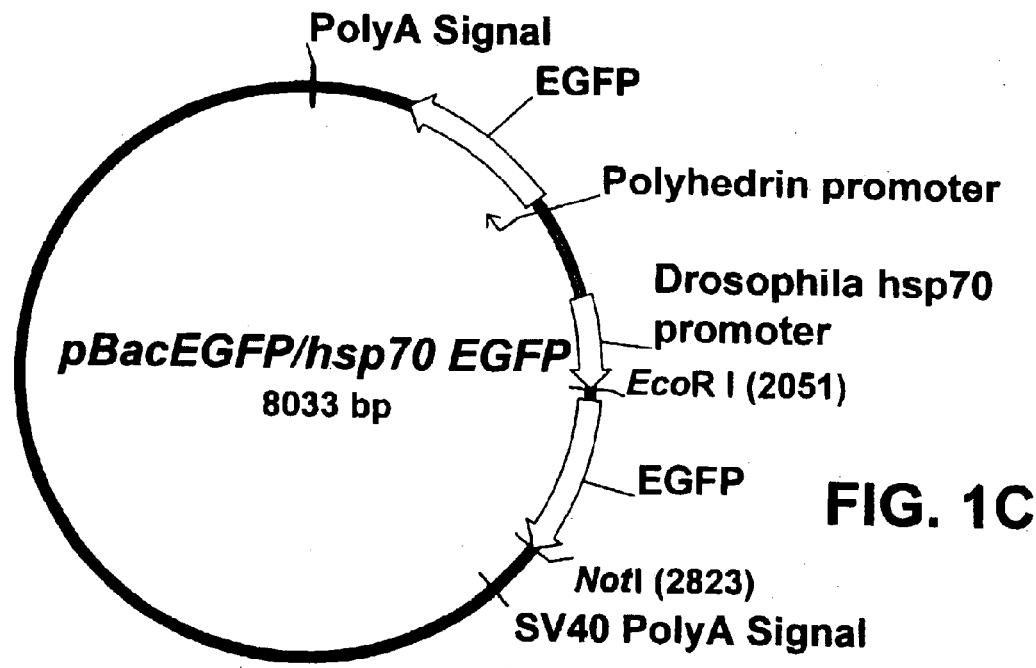
Figure 1D:
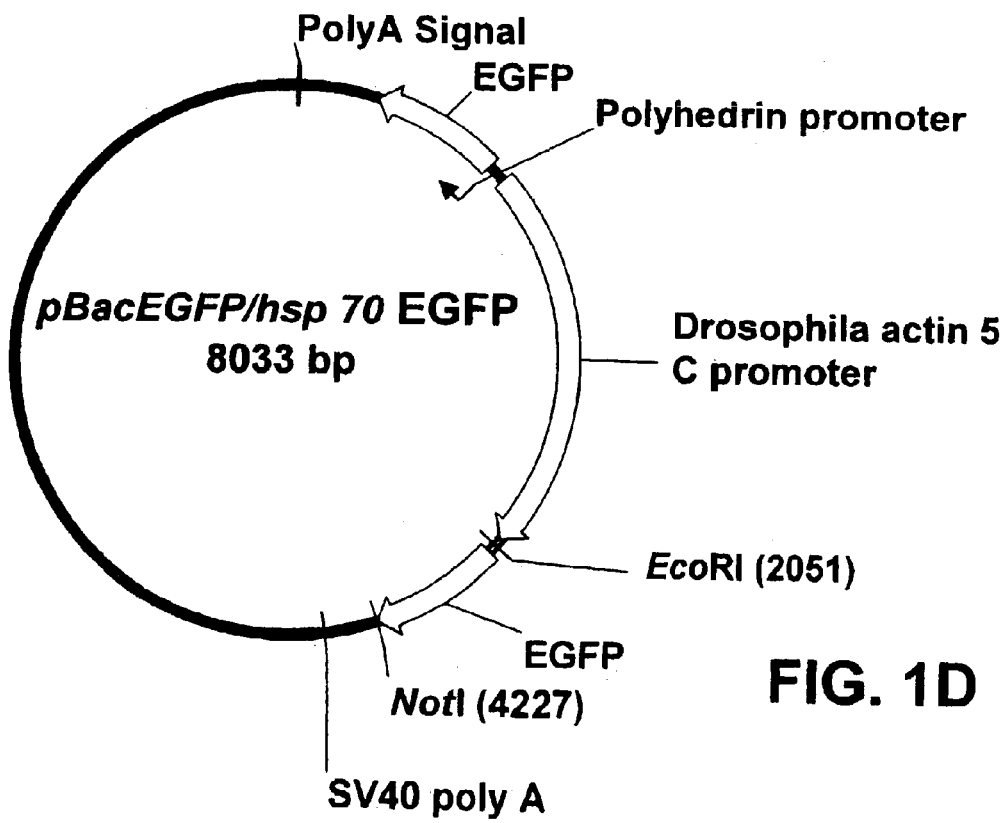

The hsp70 promoter and actin 5C promoter were incorporated into pBacEGFP in combination with SV40 polyadenylation sequences to construct pBacEGFP/hsp70 and pBacEGFP/actin5C, respectively. They both were next to and in the orientation opposite to the baculovirus polyhedrin (PH) promoter. EGFP genes (from pEGFP-1) were subcloned into pBacEGFP/hsp70 and pBacEGFP/actin5C at Eco RI and Not I sites to provide pBacEGFP/hsp70 EGFP and pBacEGFP/actin5C EGFP (See FIGS. 1(C) and (D)). The baculovirus transfer vectors as constructed contain the exogenous promoters next to and in the same orientation with the polyhedrin promoter, next to the poly A in the orientation opposite to the polyhedrin promoter, and next to the poly A in the same orientation with the polyhedrin promoter. It was found that the position of either the hsp70 or actin 5C promoter next to and in the orientation opposite to the polyhedrin promoter could exhibit high EGFP expression. However, other arrangements of the promoters will also work.

Recombinant baculoviruses, BacEGFP/hsp70EGFP and BacEGFP/actin5C EGFP, were generated by using BacPAK system (Clontech). Viruses were further amplified by propagation in Sf21 cells, which were maintained at 27° C. in Grace's medium with a 10% fetal bovine serum (Life Technologies).

When Sf21 cells were infected with recombinant viruses, EGFP expression was detected by fluorescence microscopy. It was convenient to pick up a single green clone and count virus titers by utilizing EGFP as a fluorescent marker.

Example 5

Transduction of Non-Permissive Insect Cells by Recombinant Baculovirus and Detection of Target Protein Expression S2 cells were seeded in 24-well culture plates at $10^6$ cells per well and maintained at 23.5° C. in a modified M3 medium (Sigma) supplemented with 10% fetal bovine serum (Life Technologies). S2 cells were incubated with the individual viruses as constructed in Example 3 with shaking at 40 rpm for 1 hr at room temperature at the multiplicity of infection (moi) indicated. After removal of the virus, the fresh medium was replaced and S2 cells were incubated at 23.5° C. EGFP expression was monitored by fluorescence microscopy after 36 hours post-infection in the S2 cells which were infected with BacEGFP/hsp70EGFP and BacEGFP/actin5C EGFP at moi of 10 plaque forming units (pfu) per cell, respectively. No EGFP was detected in the S2 cells infected with BacEGFP because the viral polyhedrin promoter is not active in S2 cells.

For Western blot analysis, cell pellets were added into the sampling buffer (2% SDS, 10% glycerol, 6.25 mM Tris), boiled, and analyzed by denaturing polyacrylamide gels, and proteins were transferred to the Immobilon-P transfer membranes (Millipore) by a semidrier (Bio-Rad) and immunoblotted using standard methods. EGFP was detected by a GFP polyclonal antibody (Clontech, catalog number: 8363–2). EGFP expression was detected by infecting cells with BacEGFP/hsp70 EGFP and BacEGFP/actin5C EGFP but not detected by-infecting cells with BacEGFP. It was found that the hsp70 promoter has higher expression levels than the actin 5C promoter in this system although the actin 5C promoter is more active than the hsp70 promoter from transfection data. This result indicates that EGFP under the control of a hsp70 promoter or an actin 5C promoter would express EGFP by baculovirus-mediated gene delivery.

Infection Efficiencies of Baculovirus-Mediated Gene Expression

To assay the dose responses of baculovirus-mediated gene expression, S2 cells were exposed to increasing doses of BacEGFP/hsp70 EGFP and detected by confocal microscopy and flow cytometry 36 hours post-infection.

In a confocal microscopic examination, S2 cells infected with BacEGFP/hsp70 EGFP at moi 1, 10, 100 and 200 were collected and incubated in a polylysin-coated micro slide for 30 min. Cells were washed with PBS twice, covered with cover glasses and sealed by mounting medium (2% n-propyl gallate in 6% glycerol in PBS, pH 8,0). EGFP expression were detected by Leica TCS NT confocal microscopy.

In a flow cytometry assay, S2 cells were harvested and re-suspended in PBS. Data collection was performed on Becton Dickinson FACSCalibar flow cytometer. A Linear-Flow™ Green Flow Cytometry Intensity Calibration Kit (Molecular Probe's L-14822) was used as a calibrated intensity standard for use in flow cytometry experiments. As a reference standard, EGFP expressions in S2 cells was quantified to be relative fluorescence intensities.

These results of confocal microscopy and flow cytometry experiments (averages of three independent infections) indicate the infection efficiency would reach the maximum (95%-96%) at moi of 100 pfu per cell and infection efficiencies did not increase with higher moi. Thus, infection with 100 moi is enough to express the maximum protein in S2 cells.

Time Course Study of Baculovirus-Mediated Gene Expression

To assay the time course of baculovirus-mediated gene expression, S2 cells were exposed to BacEGFP/hsp70 EGFP and detected with increasing hours. S2 cells were exposed to the BacEGFP/hsp70 EGFP virus for 1 hr at 25° C. with shaking at 40 rpm, followed by harvesting cells at various time points and quantifying the harvested cells by flow cytometry (Table 1A). Both the average EGFP expression and the infection efficiency peaked at 24–36 hours post-infection and dropped after 60 hours post-infection. The decrease of average EGFP expression and infection efficiency with time could be accounted for by the lack of viral DNA replication with cell division (Carbonell et al., 1985, J. Virol. 56, 153–160.). Thus, the percentage of cells expressing EGFP decreased with time. According to the results of both the average of EGFP expression by flow cytometry and the cell growth by trypan blue assay, it could be concluded that the EGFP expression level would reach the maximum at 36 hr.

Baculovirus-Mediated Gene Delivery to S2 Cells is Non-Lytic

*S. frugiperda* (fall armyworm) Sf9 cells were maintained at 27° C. in Grace's medium with 10% fetal bovine serum (Life Technologies). High Five™ cells were maintained at 27° C. in a High Five™ cell culture medium (Invitrogen). Sf21, Sf9 and High Five™ cells were incubated with the BacEGFP/hsp70 EGFP virus at 100 moi. It was found that the host cells Sf21, Sf9 and High Five™ infected with the baculovirus underwent a lytic pathway.

To detect whether the infection of baculovirus in S2 cells undergo a Lytic pathway or not, S2 cells were exposed to the BacEGFP/hsp70 EGFP virus at 100 moi and measurement of the S2 cell survival rate was by trypan blue assay. It was found that the cell survival and cell growth of S2 cells infected with baculovirus was not interfered with even over 30 days. Although the Sf2, Sf9 and High Five™ cells harboring the baculovirus were lytic, the S2 cell harboring the baculovirus is non-lytic.

Example 6

Superinfection of *Drosophila* S2 Cells with recombinant Baculoviruses

To estimate whether *Drosophila* S2 cells infected with one baculovirus would shut down the infection and protein expression of another baculovirus or not, *Drosophila* S2 cells were co-infected with BacEGFP/hsp70 dCdc2 (HA tagged), BacEGFP/hsp70 ena, and BacEGFP/hsp70 EGFP at MOIs of 100 or sequentially infected by the aforementioned three viruses at 4-h intervals. EGFP was detected by a GFP polyclonal antibody (Clontech, catalog number: 8363–2); HA epitope was detected by an HA monoclonal antibody (BAbCO, catalog number: MMS-101R); ena was detected by ena polyclonal antibody (Juang J L and F M Hoffmann; 1999, Oncogene 37:5138–5147). After 36 hr incubation, cell extracts were analyzed by Western blots probed with antibodies directed against EGFP, HA, and ena. No obvious differences were found between single baculovirus infection, confection or infection sequential with two baculovirus as in S2 cells. No interference to protein expression was found by successive infection with two baculoviruses. BacEGFP/hsp70 DsRed and BacEGFP/hsp70 EGFP were either co-infected or sequentially infected at 4-h intervals. Results of confocal microscopy of fluorescent target gene co-expression in S2 cells show indicate that more than 96% of the cells demonstrated co-expression of two proteins either by co-infection or by superinfection of recombinant viruses.

In summary, a comparison between the expression system as illustrated in this example and the conventional system is listed below:

| Expression System | Conventional baculovirus in lepidoptran host cells | Baculovirus in mammalian cells according to Examples 1–3 | Baculovirus in S2 cells according to Examples 4–6 |
| --- | --- | --- | --- |
| Plaque assay | Anti-gp64 selection/neutral red | EGFP selection | EGFP selection |
| Expression promoter | Polyhedrin | CMV | Drosophila hsp 70 |
| Cell lysis | Yes | No | No |
| Protein yield | High | N.D. | High |
| Superinfection | No | Yes | Yes |

Example 7

Comparison of Protein Expression Among S2, Sf9, Sf21 and High Five™ Cells

The amount of protein expressed by the methods described herein compared with common baculovirus expression system was quantified. $10^6$ S2 cells were infected with BacEGFP/hsp70 EGFP at moi 100 and incubated for 36 hours. Half of the S2 cells were collected for measuring the total proteins by DC Protein Assay (BIO-RAD) and another half was used to detect EGFP expressions in S2 by Western blot. As quantitative protein standards, 333 ng, 100 ng, 33.3 ng and 10 ng GFP (Clontech) were loaded in the gel. Western blot results were analyzed by FUJIFILM Phospho-Image FLA-2000. The EGFP expression efficiency is the amount of EGFP over the amount of the total cell protein. Sf9, Sf21 and High Five™ cells were also treated in the same manner but incubated for 3 days to evaluate the maximum protein expression. All data were repeated 3 times.

To quantify the EGFP expression in these cell lines, 53 ng protein of interest was obtained from $5 \times 10^5$ S2 cells infected with 100 moi BacEGFP/hsp70 EGFP for 36 hr, while 17 ng, 30 ng and 71 ng proteins were obtained from $10^5$ Sf9, Sf21, and High Five™ cells infected with 100 moi BacEGFP for 72 hours. In a comparison of the yields of proteins expressed in the S2, Sf9, Sf21 and High Five™ cells, the yield of EGFP in the S2 cells is more than in Sf 9 and Sf21 cells but less than in High Five™ cells. The protein expression in the S2 cells is comparable to Sf9, Sf21 and High Five™ cells.

All of the literature and publications as recited in the context of the present disclosure are incorporated herein by reference in their entirety.

The examples provided herein are not meant to be exclusive. Many other variations and modifications of the above described embodiments of the present invention would be carried out without departing from the spirit and scope of this invention. Accordingly, other embodiments are within the scope of the following claims.

What is claimed is:

1. A recombinant baculovirus comprising:
   a first nucleic acid sequence encoding a detectable marker operably linked to a first promoter, wherein the first promoter is active in a permissive cell and inactive in a non-permissive cell; and
   a second nucleic acid sequence which includes an exogenous nucleic acid sequence operably linked to a second promoter, wherein the second promoter is active in the non-permissive cell and inactive in the permissive cell.

2. The recombinant baculovirus of claim 1, wherein the first promoter is inactive and the second promoter is active in a mammalian cell.

3. The recombinant baculovirus of claim 1, wherein the first promoter is inactive and the second promoter is active in a human cell.

4. The recombinant baculovirus of claim 1, wherein the first promoter is inactive and the second promoter is active in a primary human cell.

5. The recombinant baculovirus of claim 1, wherein the first promoter is inactive and the second promoter is active in a non-permissive insect cell.

6. The baculovirus of claim 1, wherein the first promoter is a viral polyhedrin promoter.

7. The recombinant baculovirus of claim 1, wherein the first promoter is a P10 promoter.

8. The recombinant baculovims of claim 1, wherein the detectable marker is a fluorescent protein.

9. The recombinant baculovirus of claim 2, wherein the second promoter is a CMV promoter or an SV40 promoter.

10. The recombinant baculovirus of claim 5, wherein the first promoter is inactive and the second promoter is active in a non-permissiVe Drosophila cell.

11. The recombinant baculovirus of claim 5, wherein the second promoter is a heat shock protein promoter, an Orgyla pseudotsugata nuclear polyhedrosis virus immediate-early promoter, a metallothionein (MT) promoter, or an actin 5C promoter.

12. The recombinant baculovims of claim 8, wherein the fluorescent protein is green fluorescent protein (GFP), enchanced GFP (EGFP), enhanced yellow fluorescent protein (EYFP), enhanced cyan fluorescent protein (ECFP), enhanced blue fluorescent protein (EBFP), or Discosoma red fluorescent protein (DsRed).

13. A method for selecting a viral plaque for infection of non-permissive cells, comprising:
   providing a recombinant baculovirus that comprises a first nucleic acid sequence encoding a detectable marker operably linked to a first promoter, wherein the first promoter is active in a permissive host cell culture and is inactive in a non-permissive cell; and a second nucleic acid sequence comprising an exogenous nucleic acid sequence operably linked to a second promoter, wherein the second promoter is active in the non-permissive cell and inactive in the permissive cell;
   infecting the permissive host cell culture with the recombinant baculovirus; and
   identifying a viral plaque by detecting expression of the detectable marker, thereby selecting a viral plaque for infection of non-permissive cells.

14. The method of claim 13, wherein a recombinant baculovirus is provided in which the first promoter is inactive and the second promoter is active in a mammalian cell.

15. The method of claim 13, wherein a recombinant baculovirus is provided in which the first promoter is inactive and the second promoter is active in non-permissive insect cell.

16. The method of claim 13, wherein a recombinant baculovirus is provided in which the first promoter is a viral polyhedrin promoter or a P10 promoter.

17. The method of claim 13, wherein a recombinant baculovirus is provided in which the second promoter is a CMV promoter, a SV40 promoter, a heat shock protein promoter, an OPIE2 promoter, a MT promoter, or an actin 5C promoter.

18. The method of claim 14, wherein a recombinant baculovirus is provided in which the first promoter is inactive and the second promoter is active in a human cell.

19. The method of claim 15, wherein a recombinant baculovirus is provided in which the first promoter is inactive and the second promoter is active in a non-permissive Drosophila cell.

20. A method for producing a protein product in a non-permissive cell, comprising:

providing a recombinant baculovirus that comprises: a first nucleic acid sequence encoding a detectable marker operably linked to a first promoter, wherein the first promoter is active in a permissive host cell culture and is inactive in a non-permissive cell; and a second nucleic acid sequence comprising an exogenous nucleic acid sequence encoding the protein product operably linked to a second promoter, wherein the second promoter is active in the non-permissive cell and is inactive in the permissive host cell culture;

infecting the permissive host cell culture with the recombinant baculovirus;

selecting a viral plaque by identifying expression of the detectable marker;

amplifying the baculovirus by growing the baculovirus from the selected viral plaque; and infecting a non-permissive cell with the amplified baculovirus, wherein the non-permissive cell thereby produces the protein product encoded by the exogenous nucleic acid sequence and wherein the non-permissive cell does not express the detectable marker.

21. The method of claim 20, further comprising the step of re-infecting the non-permissive cell with a recombinant baculovirus.

22. The method of claim 20, wherein the non-permissive cell infected is a mammalian cell.

23. The method of claim 20, wherein the non-permissive cell infected is an insect cell.

24. The method of claim 20, wherein the non-permissive cell is infected in vitro.

25. The method of claim 20, wherein the non-permissive cell is infected in vivo.

* * * * *

SEQUENCE LISTING

<160> NUMBER OF SEQ ID NOS: 3

<210> SEQ ID NO 1
<211> LENGTH: 30

-continued

<212> TYPE: DNA
<213> ORGANISM: Artificial Sequence
<220> FEATURE:
<223> OTHER INFORMATION: oligonucleotide for PCR

<400> SEQUENCE: 1
caggatccgc caccatggtg agcaagggcg                            30

<210> SEQ ID NO 2
<211> LENGTH: 33
<212> TYPE: DNA
<213> ORGANISM: Artificial Sequence
<220> FEATURE:
<223> OTHER INFORMATION: oligonucleotide for PCR

<400> SEQUENCE: 2
agcaattaat taatgaacat gtcgagcagg tac                        33

<210> SEQ ID NO 3
<211> LENGTH: 33
<212> TYPE: DNA
<213> ORGANISM: Artificial Sequence
<220> FEATURE:
<223> OTHER INFORMATION: oligonucleotide for PCR

<400> SEQUENCE: 3
gtacctgctc gacatgttca ttaattaatt gct                        33